United States Patent [19]

Bauer et al.

[11] 4,190,583

[45] Feb. 26, 1980

[54] PROCESS FOR THE PREPARATION OF 3,4-METHYLENEDIOXYMANDELIC ACID

[75] Inventors: Kurt Bauer, Holzminden; Reiner Mölleken, Galmback Ortst. Warbsen, both of Fed. Rep. of Germany

[73] Assignee: Haarmann & Reimer GmbH, Holzminden, Fed. Rep. of Germany

[21] Appl. No.: 964,553

[22] Filed: Nov. 29, 1978

[30] Foreign Application Priority Data

Dec. 7, 1977 [DE] Fed. Rep. of Germany ....... 2754490

[51] Int. Cl.$^2$ .......................................... C07D 317/44
[52] U.S. Cl. .............................................. 260/340.5 R
[58] Field of Search ................................. 260/340.5 R

[56] References Cited

U.S. PATENT DOCUMENTS 3,970,703  7/1976  Kitamura et al. ............. 260/340.5 X

OTHER PUBLICATIONS

Barthel et al., Journ. Org. Chem., 19 (1954), pp. 485–489.
Werber et al., Gazz. Chim. Ital. 96 (4), 1966, p. 465.

*Primary Examiner*—Ethel G. Love
*Attorney, Agent, or Firm*—Sprung, Felfe, Horn, Lynch & Kramer

[57] ABSTRACT

Process for the preparation of 3,4-methylenedioxymandelic acid, wherein glyoxylic acid is reacted with 1,2-methylenedioxybenzene in a strongly acid medium.

2 Claims, No Drawings

PROCESS FOR THE PREPARATION OF 3,4-METHYLENEDIOXYMANDELIC ACID

The invention relates to a new process for the preparation of 3,4-methylenedioxymandelic acid.

3,4-Methylenedioxymandelic acid has hitherto been prepared from piperonal, via piperonal cyanohydrin, by processes analogous to the customary preparation process for mandelic acid and mandelic acid derivatives (Chemisches Zentralblatt 1909, pages 1927-28). However, because of the expensive starting material piperonal which is required, this process is of no interest industrially.

It has now been found that 3,4-methylenedioxymandelic acid can be prepared in a simple manner and in excellent yields starting from the cheaper, readily accessible starting materials, 1,2-methylenedioxybenzene and glyoxylic acid, when 1,2-methylenedioxybenzene is reacted with glyoxylic acid in a strongly acid medium.

The acid strength of the glyoxylic acid when it is employed in the form of the monohydrate or semihydrate is in itself sufficient to catalyse the reaction. However, because of the reaction temperatures of about 60°-80° C. advisable for the reaction, considerable amounts of bis-(3,4-methylenedioxyphenyl)-acetic acid are formed. This by-product is formed by the addition of a further 1,2-methylenedioxybenzene molecule onto the desired 3,4-methylenedioxymandelic acid.

It has therefore proved to be advantageous to add as catalysts acids which are stronger than glyoxylic acid and which are inert under the reaction conditions, for example strong mineral acids, such as 85% strength phosphoric acid, 70% strength sulphuric acid or concentrated or gaseous hydrochloric acid, or strong organic acids, such as trifluoroacetic acid and dichloroacetic acid. By adding these acids, the reaction temperature can be lowered to 0° to 60° C. and the formation of bis-(3,4-methylenedioxyphenyl)-acetic acid can thereby be greatly reduced. Acids which are stronger than glyoxylic acid are understood, in the scope of the process according to the invention, as those acids which have a dissociation constant in water of over $4.74 \times 10^{-4}$ (dissociation constant of glyoxylic acid), preferably over $10^{-3}$.

If the glyoxylic acid is employed in the form of aqueous solutions, for example the commercially available 50% strength aqueous solution, to achieve the required acid strength it is necessary to use a relatively large amount of the strong mineral acids and organic acids or, if the acids themselves should contain water, to use acids of relatively high concentration, in order to compensate the dilution effect of the water.

Since the starting materials are frequently immiscible with one another or insoluble in one another and, because of its low solubility, the reaction product is predominantly obtained in the crystalline form, it is advantageous to stir the heterogeneous reaction mixture.

In order to preserve the stirrability it can be advantageous to employ substantially larger amounts of the strong acid then are necessary to achieve the acid strength. The disadvantage that a relatively large proportion of the reaction product also remains dissolved in this relatively large amount of acid after filtering off the reaction product can be compensated for by re-using the acid, if appropriate after concentrating.

The reaction is preferably carried out without a solvent. However, in some cases the addition of a solvent, preferably a polar solvent, which is stable under the reaction conditions, for example formic acid or acetic acid, can have an advantageous effect on the course of the reaction, as long as the acid strength necessary for catalysing the reaction is maintained, since the solvent acts as a solubilising agent between the different phases. Particularly suitable solvents are organic acids simultaneously acting as a strong acid, such as trifluoroacetic acid and dichloroacetic acid.

The starting compounds 1,2-methylenedioxybenzene and glyoxylic acid are preferably employed in equimolar amounts.

The course of the reaction according to the invention is surprising, since it is known, from Gazz. Chim. Ital. 96 (4), 465 (1966), that the reaction of glyoxylic acid alkyl esters with alkyl-substituted aromatic compounds in a strongly acid medium indeed leads to mandelic acid derivatives, but with alkoxy-substituted aromatic compounds, such as veratrole, gives only diphenylacetic acid derivatives.

3,4-Methylenedioxymandelic acid is, inter alia, an important starting material for the preparation of the valuable aroma substance piperonal. Piperonal is prepared from 3,4-methylenedioxymandelic acid by oxidative decarboxylation (see Current Sci. (India) 27, 22 (1958)).

EXAMPLE 1

46 g (0.5 mol) of glyoxylic acid monohdrate, 61 g (0.5 mol) of 1,2-methylenedioxybenzene and 200 g (1.74 mols) of 85% strength phosphoric acid are brought together at 25° C. and the mixture is stirred for 5 hours. The temperature thereby rises to 38° C. In order to preserve the stirrability of the reaction mixture, 40 ml of water are added. After 5 hours, a further 160 ml of water are added, the mixture is further stirred for 10 minutes and the crystals obtained are filtered off. The crystals are dissolved in 650 ml of water and 100 ml of toluene at 85° C. and the phases are separated. After washing the toluene phase several times with 20% strength sodium hydroxide solution and distilling off the solvent, 7.1 g of 1,2-methylenedioxybenzene are recovered. After cooling the aqueous phase to room temperature, 57.6 g of 3,4-methylenedioxymandelic acid crystallise out, and after concentrating the mother liquor a further 8.3 g of 3,4-methylenedioxymandelic acid crystallise out. The yield of 3,4-methylenedioxymandelic acid is 76.1% of theory, relative to 1,2-methylenedioxybenzene reacted. It can be increased further by working up the strongly acid filtrate of the reaction mixture. However, since the working up is very expensive, it is more advantageous to concentrate the acid filtrate and re-use it.

EXAMPLE 2

200 g of 90% strength sulphuric acid are added dropwise to a mixture of 148 g (1 mol) of 50% strength aqueous glyoxylic acid and 122 g (1 mol) of 1,2-methylenedioxybenzene at 5° C. in the course of 40 minutes, whilst stirring. After stirring the mixture for a further 6 hours, 500 g of ice-water are added and the mixture is stirred for a further 10 minutes. The crystals which have precipitated are filtered off and worked up as in Example 1. 6.1 g of 1,2-methylenedioxybenzene are recovered from the toluene phase. 167.3 g of 3,4-methylenedioxymandelic acid, corresponding to a yield of 85.3% of theory, relative to 1,2-methylenedioxybenzene reacted, are obtained from the aqueous phase.

EXAMPLE 3

A mixture of 92 g (1 mol) of glyoxylic acid monohydrate and 122 g (1 mol) of methylenedioxybenzene is stirred at 80° C. for 4 hours, 700 ml of water and 150 ml of toluene are then added and the phases are separated. After cooling the aqueous phase to room temperature, 44.7 g of 3,4-methylenedioxymandelic acid crystallise out, and after concentrating the aqueous phase a further 17.3 g of 3,4-methylenedioxymandelic acid crystallise out. After extracting the toluene phase by shaking with 100 ml of 20% strength sodium hydroxide solution and distilling off the toluene, 10.5 g of unreacted 1,2-methylenedioxybenzene are obtained. The yield of 3,4-methylenedioxymandelic acid is 34.6% of theory, relative to 1,2-methylenedioxybenzene reacted.

EXAMPLE 4

39 g (0.424 mol) of glyoxylic acid monohydrate are dissolved in 126 g of trifluoroacetic acid, and 51.7 g (0.424 mol) of 1,2-methylenedioxybenzene are added at 20° C. The initially homogeneous mixture is stirred at 20° C. for 3.5 hours. The crystals which have precipitated are then filtered off and worked up as described in Example 1. 10 g of bis-(3,4-methylenedioxyphenyl)-acetic acid are obtained from the toluene phase. 62.2 g of 3,4-methylenedioxymandelic acid are obtained from the aqueous phase. This corresponds to a yield of 75% of theory, relative to 1,2-methylenedioxybenzene employed. The yield can be increased by working up the strongly acid filtrate of the reaction mixture. However, it is more advantageous to concentrate the acid filtrate and re-use it.

If, instead of glyoxylic acid monohydrate, an equivalent amount of 50% strength aqueous glyoxylic acid is employed and the mixture is stirred for 6 hours instead of 3.5 hours, 8.58 g of bis-3,4-methylenedioxyphenylacetic acid are obtained from the toluene phase and 73.4 g of 3,4-methylenedioxymandelic acid, corresponding to a yield of 76.3% of theory, relative to 1,2-methylenedioxybenzene employed, are obtained from the aqueous phase.

We claim:

1. A process for the preparation of 3,4-methylenedioxymandelic acid, which comprises reacting glyoxylic acid with 1,2-methylenedioxybenzene in the presence of a strong acid having a dissociation constant in water of over $4.74 \times 10^{-4}$.

2. A process as claimed in claim 1, wherein the reaction is carried out in the presence of phosphoric acid, sulphuric acid, gaseous or concentrated hydrochloric acid, trifluoroacetic acid or dichloroacetic acid.

* * * * *